United States Patent [19]

Scolastico et al.

[11] Patent Number: 4,699,901
[45] Date of Patent: Oct. 13, 1987

[54] DIACYL DERIVATIVES OF GLYCERYLPHOSPHORYLCHOLINE, THEIR PREPARATION, AND ANTIHYPERLIPIDEMIC COMPOSITIONS

[75] Inventors: Carlo Scolastico, Milan; Giovanni Tronconi, Vimodrone, both of Italy

[73] Assignee: Neopharmed SpA, Baranzate di Bollate, Italy

[21] Appl. No.: 803,474

[22] Filed: Dec. 2, 1985

[30] Foreign Application Priority Data

Dec. 5, 1984 [IT] Italy .................................. 23896 A/84

[51] Int. Cl.$^4$ .................. C07F 9/58; A61K 31/685
[52] U.S. Cl. ................................. 514/77; 546/2; 546/22; 558/169; 556/26
[58] Field of Search .............. 514/77; 546/2, 22

[56] References Cited

PUBLICATIONS

Tanaka, Chem. Abs. 78, 97970n.

*Primary Examiner*—Mark L. Berch
*Attorney, Agent, or Firm*—Murray and Whisenhunt

[57] ABSTRACT

The diacylesters, particularly bis(pyridyl-3-carboxilate) of glycerylphosphorylcholine, both optically active L(alpha) or racemic D, L(alpha) and their complexes having general formula:

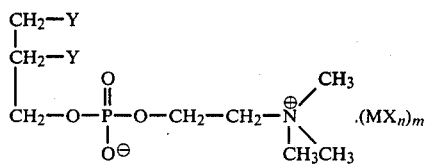

wherein:
Y represents

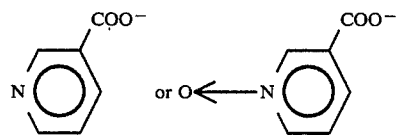

M represents Ca, Mg, Al, Zn
X represents a halogen, particularly chlorine, n=2,3 ed m=0,1 are anti-dislipemic and cerebroactive agents.

Their preparation takes place through acylation with an anhydride of a complex of glycerylphosphorylcholine with calcium or zinc chloride.

12 Claims, No Drawings

DIACYL DERIVATIVES OF GLYCERYLPHOSPHORYLCHOLINE, THEIR PREPARATION, AND ANTIHYPERLIPIDEMIC COMPOSITIONS

The present invention relates to bis(pyridyl-3-carboxylate) esters of optically active L(alpha) or racemic D,L(alpha) glycerylphosphorylcholine and to the respective complexes having general formula:

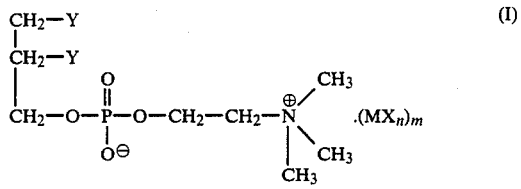

wherein:
Y represents

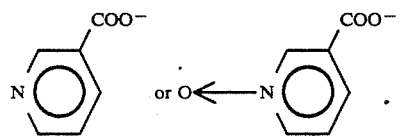

M represents Ca, Mg, Al, Zn
X represents a halogen, particularly chlorine, n=2,3 ed m=0,1
These esters and their complexes (occurring when M=1 in the formula I) are anti-dislipemic and cerebroactive agents.

The present invention relates furthermore to the preparation of the esters and complexes of formula (I).

In a number of investigations it has been demonstrated that the oral administration of lecithin to hyperlipoproteinemic patients causes a relevant reduction of the plasma triglycerides (Cobb M., Turkki P., Linscheer W., Raheja K., Nutr. Metab, 24: 228–237, 1980; Ditschuneit H., Klor H. U., Ditschunei H. H., Phosphatidylcholine: Biochemical and Clinical Aspects of Essential Phospholipids, New York, Springer-Verlag 1976: 98–114: Svanverg U., Gustfson A., Ohlson R., Nutr. Metab. 17; 338–346 1974).

In a recent investigation (Childs M. T. Bowling H. A., Ogilvie J. T., Hazzard W. R., Albers J. H. Atherosclerosis 38: 217–228, 1981) it has been demonstrated the effect of the lecithin on the hypercholesterolemy with a remarkable increase of the HDL-cholesterol.

Like conclusion have been attained by other researchers (Wong E. K., Nicolosi R. J., Low P. A., Herd J. A., Hayer K. C. Lipids 15: 428–433 1980) after administration of phosphatidylcholine to hyperlipemic monkeys.

An anti-aterogenic action of polienoic phosphatidylcholine (glyceril phosphorylcholine Dilinoleate) has been furthermore shown with an increase of the hydrolysis of cholesteryl ester and a reduction of the synthesis of cholesteryl esters from acyl-CoA: cholesterol-acyltransferase. According to another investigation (Samochowiec L. Phosphatidylcholine: Biomedical and clinical Aspects of Essential Phospholipids, New York, Springer Verlag 1976, 211–226) these observations have been extended to rats and mini-pigs treated per os with phosphatidylcholine, wherein a significant action took place both of regression and of anti-aterogenic prevention.

The activity at the level of SNC (central nervous system) might take place since the GFC-dinicotinate can be defined as a carrier of choline with high affinity. Owing to the fact that in the Alzheimer disease the main biochemical lesion is represented by a relevant diminution of the activity of the choline acetyltransferase in the hippocampus (Bowen D. N. et al, Brain 99, 459, 1976- Lancet I, II, 1979) the administration of choline donors may compensate the reduced cholinergic activity through the stimulation to a higher activity of neurons.

Investigations carried out in old animals and with a compromised memory indicate that the relevant changes which are observed in the cholinergic mechanisms as the age advances are in part responsible of memory losses (Deutsch J. A.: Choline and Lecithin in Brain Disorders, N.Y. Raven Press 343, 1979).

However from the above panorama of the state of the art it appears that while the phosphatidylcholine was and is the subject of several investigations with respect to the normolipemizing, antiaterosclerosis activity and on the central nervous system activity, nothing has been essentially disclosed or even suggested as regards the glycerylphosphorylcholine. The esterification on industrial scale of glycerylphosphorylcholine (GFC) shows relevant difficulties owing to the poor solubility of the product in the aprotic solvents which are normally used for the O-acylation reactions (pyridine, chloroform benzene).

Although the O-diacyl derivatives of GFC are soluble in these solvents it is highly difficult to carry out the esterification reaction on broad scale in heterogeneous phase since the anhydrous GFC normally posses high viscosity which, in combination with the poor solubility, does not permit the stirring.

Furthermore the use of solid GFC is not possible since the crystallization thereof is highly difficult (N. H. Tattried, Biochemical Preparation, Vol. 6 (1958), pag. 16.

The esterification of GFC can be carried out for example in dimethylsulfoxide in the presence of ⊖CH₂—S—CH₃ (T. Warner, A. Benson, J. of Lipid Research, 18 (1977), 548). Such a sinthesys method, besides being costly and dangerous, involves relevant difficulties if used on broad scale owing to the difficulty of fully eliminating the dimethylsulfoxide. The more common esterification mehod uses the complex GFC. 3CdCl₂. With such a complex the esterification can be carried out also in the common solvents of O-acylation.

The use of CdCl₂ however renders the method scarcely suitable for the preparation of products for pharmaceutical use owing to the difficulties which are to be faced in the complete elimination of cadmium (an extremely toxic metal).

It has been now found that the problems and drawbacks above shortly mentioned are substantially solved with a process for the preparation of the esters of formula (I) wherein the glycerylphosphorylcholine is reacted with reactive derivatives of pyridin-3-carboxylic acid, characterized in that there is used as the reactant to be esterified a complex of glycerylphosphorylcholine with calcium or zinc chloride having the formula:

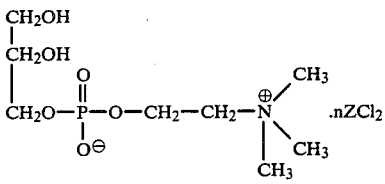

wherein Z represents Ca, Zn and n may have one of the following values: 0.5; 0.75; 1.25 and 1.5

These complexes, which are easily preparable solids, possess a satisfactory solubility as regards the reaction in common acylation solvents, which is variable with the value of n, whereby it is possible to carry out the esterificaiton reaction in these solvents.

For preparation on small scale however an anhydrous GFC can be used. The acylating agent which is preferably used is the anhydride of pyridin-3-carboxylic acid which is separately prepared or prepared in "situ" from the acyl chloride hydrochloride and from the sodium or potassium salt of pyridin-3-carboxylic acid.

The esterification is carried out with the help of a specific acylation catalyst, such as for instance 4-dimethylaminopyridine, in the presence of a tertiary amine, such as triethylamine, tributylamine, pyridine, etc. The diester obtained by using as only acylating agent the chloride of pyridyl-3-carboxylic acid hydrochloride is not pure owing to the presence of monochloroester of formula (III):

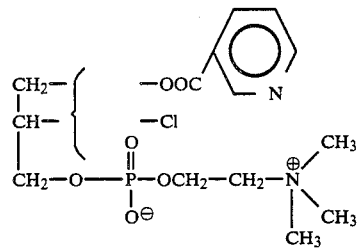

which can be also obtained quantitatively by carrying out for example the esterification at 60°-70° C. in pyridine.

In turn the esters wherein

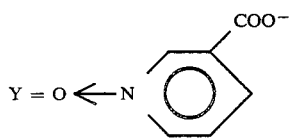

are prepared through oxidation in organic solvent, preferably chloroform, with m-chloroperbenzoic acid, of the esters of formula (I) wherein

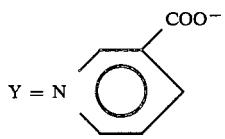

The optically active form L(alpha), or pure GFC is obtained through deacylation of phosphatidylcholine and contains $H_2O$ about 15-20%), whereas the anhydride of pyridin-3-carboxylic acid is prepared according to the ISOO method (Is. Isoo et al, Japan 6823, 626 11/10/1968: CA: 70 57688). In turn the racemic for D,L(alpha), of GFC is prepared according to the method of Mushica (Y. Mushica and coll. Chem. Pharm. Bull. 19(4), 696(1971).

EXAMPLE 1

Preparation of the L(alpha)GFC. 0.5 $CaCl_2$ complex

A solution of L(alpha) GFC (19.2% $H_2O$) (67.2 G=0.21 moles) in ethanol (150 ml) is concentrated to dryness under reduced pressure. The residue, taken with ethanol (100 ml), is added under stirring at room temperature with a solution of anhydrous $CaCl_2$ (12.38 g=0.116 moles) in ethanol (200 ml). The precipitate is filtered in nitrogen atmosphere and is dried under reduced pressure at 80°-190° C. in presence of $P_2O_5$ giving place to 58 g of L(alpha), GFC. 0.5 $CaCl_2$ (88%).

Theoretical analysis Ca %=6.41; Cl %=11.37.
Found: Ca %=6.60; Cl %=10.65.

By using the method of the previous example from 1.79 g of GFC (6.9 mmoles), $ZnCl_2$ (6.9 mmoles) there is obtained GFC 0.75 $ZnCl_2$ with a yield of 80%.

Zn % calculated=13.57 Found: Zn %=13.95.
Cl % calculated=14.81 Found: Cl %=14.97.

According to the same method by using D,L(alpha) GFC the corresponding complexes of Ca and Zn are obtained.

EXAMPLE 2

Preparation of L(alpha), GFC-bis(pyridyl-3-carboxilate) calcium salt

A suspension of sodium pyridyl-3-carboxylate (54.3 g=0.374 moles), and of chloride of pyridin-3-carboxylic acid hydrochloride (33 g=0.185 moles) in anhydrous chloroform and devoid of ethanol (350 ml) is heated to boiling under stirring and under nitrogen atmosphere for 2 hours. After filtration in an inert atmosphere the precipitate is washed with chloroform (100 ml). The solution is added with $Et_3N$ (14.6 g=0.144 moles), 4-dimethylamino pyridine (1.2 g=0.01 moles), L(alpha) GFC 0.5 $CaCl_2$ (15.5 g=0.049 moles) and then the reaction mixture is stirred at 35° C. and in an inert atmosphere for 48 hours.

The reaction mixture is thereafter extracted with water (80 ml), and then, after staying at 0° C. for 3 hours, the aqueous phase is filtered by washing the precipitate with water/ice (2×10 ml) and the water is removed through distillation under reduced pressure. The oily residue is taken with methylene chloride (50 ml), decolorized with carbon (0.5 g) and added with ethyl acetate (90 ml). There are obtained 21 g of L(alpha) GFC-bis(pyridyl-3-carboxilate), containing pyridin-3-carboxylic acid and 4-dimethylamino pyridine, as impurities.

The product is taken with absolute ethanol (50 ml) and the thus obtained solution is added with a solution of anhydrous $CaCl_2$ (5.25 g) in absolute ethanol (100 ml) and then with ethyl ether (400 ml).

After filtration under nitrogen atmosphere the purification is repeated by precipitation from ethanol/ether thus obtaining 19.25 g L(alpha) glycerylphosphorylcholine bis(pyridyl-3-carboxilate) calcium salt as a hygroscopic solid (m.p.: about 225° C. with decomposition), with a yield of 69%.

In the elemental analysis there is found:

Calculated (for $C_{20}H_{26}N_3O_8P \cdot CaCl_2$):
C=41.52%; H=4.49%; N=7.26%; P=5.36%; Cl=12.28%; Ca=6.92%.

Found C=41.20%; H=4.18%; N=7.15%; P=5.45%; Cl=11.98%; Ca=6.70%

$\lambda_{max}$ =262 nm ($H_2O$)

$E^{1\%}$=95.6 ($H_2O$)

$\epsilon$=5529

$[\alpha]_D^{20}$=+8.58 (C=2.19 in $H_2O$).

The spectroscopic characteristic data (IR,NMR) are equal to those of L(alpha) glycerylphosphorylcholine bis(pyridyl-3-carboxilate) which can be obtained in pure state through cromatography onto silica gel (0.063-0.2 Merck) using as the eluting system $CHCl_3/CH_3OH/H_2O$ (15/10/20). The product is an amorphous highly hygroscopic solid.

Calculated (for $C_{20}H_{26}N_3O_0P$): N=8.99; P=6.63
Found: N=8.75; P=6.72

IR ($CHCl_3$); 1730 (COOR); 1050; 1080 (P—O—C);

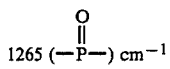
1265 (—P—) cm$^{-1}$

NMR ($D_2O$);

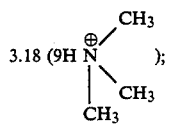
3.18 (9H)

3.64 (2H mCH$_2$—N$^\oplus$);

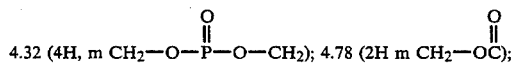
4.32 (4H, m CH$_2$—O—P—O—CH$_2$); 4.78 (2H m CH$_2$—OC);

5.70 (1H m CH—O—); 7.50 (2H m $C_3H_5N$); 8.30 (2H m$C_5H_5N$) 8.67 (2H, broad singlet, $C_5H_5N$): 8.98 (2H, d broad $C_5H_5N$). $\lambda_{max}$ =262 nm ($H_2O$). $E^{1\%}$ =122 ($H_2O$). $\epsilon$=5684.

According to the same method D, L(alpha), glycerylphosphorylcholine bis(pyridyl-3-carboxilate) has been prepared starting from D, L(alpha) GFC calcium salt.

EXAMPLE 3

Preparation of L(alpha)GFC bis(pyridyl-3-carboxilate) aluminium, magnesuium and zinc salt By treating an ethanol solution of L(alpha) GFC bis(pyridyl-3-carboxilate) with an equimolar amount of $AlCl_3$ $6H_2O$ in ethanol according to the method described in example 2 there is obtained L(alpha) GFC bis(pyridyl-3-carboxilate) aluminium salt with a yeild of 85%. Calculated (for $C_{20}H_{26}N_3O_8P$ $AlCl_3 6H_2O$): Cl %=15.03; Al %=3.81; $H_2O$=15.24%. Found: Cl %=15.5; Al %=3.70; $H_2O$=(Karl Fisher)=16.1%. According to the same method by using $MgCl_2$ there is obtained L(alpha) GFC bis(pyridyl-3-carboxilate) magnesium slat.

Calculated for $C_{20}H_{26}N_3O_8P$ $MgCl_2$; Cl %=12.63; Mg %=4.32.

Found for $C_{20}H_{26}N_3O_8P$ $MgCl_2$; Cl %=12.35; Mg %=4.60%.

According to the same method by using anhydrous $ZnCl_2$ there is obtained L(alpha) GFC bis(pyridiyl-3-carboxilate) zinc salt.

Calculated $C_{26}H_{26}N_3O_8P \cdot ZnCl_2$ Cl %=11.17

Zn %=10.83
Found for $C_{26}H_{26}N_3O_8P \cdot ZnCl_2$ Cl %=11.42

If, instead of L(alpha) GFC bis(pyridyl-3-carboxilate), D,L(alpha) GFC bis(pyridyl-3-carboxilate), is used, the corresponding slats of Al, Mg and Zn are obtained.

EXAMPLE 4

Using the methol described in example 2 from:
potassium pyridyl-3-carboxilate (62.3 g=0.387 moles)
$Et_3N$ (16.3 g=0.162 moles)
4-dimethylamino pyrdine (1.2 g=0.01 moles)
L(alpha) GFC. 0.75 $CaCl_2$ (18.5 g=0.054 moles).
there are obtained 20 g of L(alpha) glycerylphosphorylcholine bis(pyridyl-3-carboxilate calcium salt (64%).

Like results are obtained by using L(alpha) GFC 1.25 $CaCl_2$ and L(alpha GFC. 1.5 $CaCl_2$.

Using the corresponding salts of D,L(alpha) GFC, there is obtained D,L(alpha) glyceryl phosphorylcholine bis(pyridyl-2-carboxilate) calcium salt.

EXAMPLE 5

Preparation of L(alpha) glycerylphosphorylcholine bis (pyridyl-3-carboxilate) from GFC (19% $H_2O$)

From a suspension of L(alpha) GFC (19% $H_2O$) (4.4 g=0.014 moles) in pyridine (150 ml) the pyridine/water azeotrope is distilled at room pressure and under nitrogen atmosphere.

After cooling, still under stirring at 40° C. there are added: the anhydride of pyridin-3-carboxylic acid (12.72 g=0.056 moles) and 4-dimethylaminopyridine (3.3 g=0.028 moles) and then is stirred at 40° C. for 16 hours. Ethanol is added (3.5 ml), and then ethyl ether (300 ml). After decantation the residue is purified by cromatography on silica thus obtaining pure L(alpha) glycerylphosphorylcholine bis(pyridyl-3-carboxilate) (5 g=76.4%).

According to the same method but using D,L(alpha) GFC there is obtained D,L(alpha) glycerylphosphorylcholine bis(pyridil-3-carboxilate).

EXAMPLE 6

Preparation of L(alpha)GFC bis (pyridyl-3-carboxilate)-di-N-oxide

To a solution of L(alpha) GFC bis(pyridyl-3-carboxilate) (1.07 g=2.3 mmoles) in chloroform (30 ml) there is added a solution of m-chloroperbenzoic acid (1.03 g=6 mmoles) in chloroform (10 ml). The mixture is kept on standing at 25° C. for 16 hours, then is concentrated under reduced pressure to a small volume (about 7 ml). Methanol (2 ml) is added and the mixture is purified by chromatography on silica by eluting with chloroform/methanol/water (15/2/2).

There are obtained 0.85 g of L(alpha) GFC bis(pyridyl-3-carboxilate)-di-N-oxide in pure form (amorphous solid).

NMR ($D_2O$); 3.20 (9H; N$^\oplus$(CH$_3$)$_3$); 3.64 (m 2H; CH$_2$N$^\oplus$);

4.32 (m, 4H CH$_2$—O—P—OCH$_2$); 4.78 (m 2H; CH$_2$-O) 5.73 (m 1H; CH-O) 7.75 (t,

2H; $C_5H_5N$→O): 8.30 (m, 2H, $C_5N$→O); 8.55 (d, 2H, $C_5H_5N$→O); 8.85

(d, 2H,$C_5H_5N$→O);

IR (KBr): $\nu$=1280 (N→O) cm$^{-1}$.

According to the same method but using D, L(alpha) GFC bis(pyridyl-3-carboxilate) there is obtained D, L(alpha) GFC bis (pyridyl-3-carboxilate)-di-N-oxide.

The esters of formula (I) have been tested from the toxicological and pharmacological point of view.

As regards the acute toxicity it has been found that in the mice by endoperitoneal route the LD$_{50}$ is greater than 2000 mg/kg.

Pharmacological activity

The bis(pyridyl-3-carboxilate) esters of formula (I) show an antidislipemic activity higher than that of nicotinic acid. Such an activity is demonstrated for the optically active form L(alpha) by the 50% inhibition cholesterol and of triglycerides at the minimum dose of 37.5 mg/kg p.os, according to the hyperlipidemie test induced in the rat by the administration of Triton WR 1330 (F. Byrs, Experientia, 97, 117, (1953). The normolipemizing activity was confirmed also in subacute tests wherein the rats subjected to the hypercholesterolic diet of Nath (Nath et al. 1979) where treated for 21 consecutive days.

In the treated animals there occurred a significant inhibition of the parameters relating to the lipidic picture, both at the liver level and at the plasma level.

On an experimental model (Mantione C. R. et al. Science 213, 579, 1981) reproducing in the mouse the colingeric presinaptic neurochemical damage of the patients suffering from Alzheimer disease, the administration of L(alpha) bis(pyridil-3-carboxilate) calcium salt inhibits, in a dose-answer form, the regional diminution of the levels of acetylcholine in the cortex. The bis(pyridyl-3-carboxilate) or GFC thus shows, with respect to the phosphatidylcholine, the following advantages:

(1) Water solubility permitting the administration of the drug by parenteral route and ensuring a better bioavailability when it is administered by oral route.

(2) Activity at doses far less than those of phosphatidylcholine with a better compliance of the patients.

The compounds of the present invention are the active ingredient in the preparation of pharmaceutical compositions for the oral, intravenous and intramuscular administration.

The daily posology for the oral form, possibly with gastric protection, is of 200–1200 mg, whereas that for the intravenous and parenteral route is of 500–1000 mg.

The pharmaceutical compositions are formulated with the excipients, vehicles, solvents, etc. which are commonly used in the pharmaceutical field and prepared according to the normal pharmaceutical technologies.

I claim:

1. Dyacil derivatives of optically active or racemic glycerylphosphorylcholine having the formula:

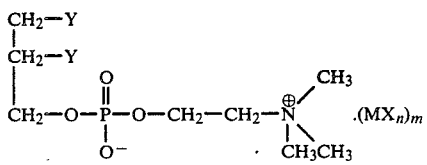

wherein:

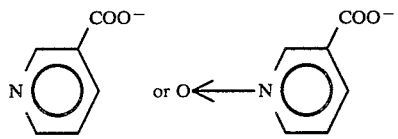

Y represents

M represents Ca, Mg, Al or Zn,

X represents a halogen, n=2 or 3, and m=0 or 1.

2. Bis(pyridyl-3-carboxilate) ester of glycerylphosphorylcholine according to claim 1.

3. Bis(pyridyl-3-carboxilate) ester of gylcerylphosphorylcholine calcium salt, accoring to claim 1.

4. Bis(pyridyl-3-carboxilate) ester of glycerylphosphorylcholine aluminium salt, according to claims 1.

5. Bis(pyridyl-3-carboxilate) ester of glycerylphosphorylcholine magnesium salt according to claim 1.

6. Bis(pyridyl-3-carboxilate) ester of glycerylphosphorylcholine zinc salt, according to claim 1.

7. Bis(pyridyl-3-carboxilate) ester of glycerylphosphorylcholine N-oxide, according to claim 1.

8. A pharmaceutical composition comprising an anti-hyperlipidemically effective amount of a diacylester of glycerylphosphorylcholine according to claim 1 in combination with pharmaceutically acceptable excipients, vehicles, solvents or mixtures thereof.

9. Pharmaceutical composition according to claim 8, characterized by being in form suitable for the administration by oral route.

10. The compound according to claim 1, wherein said halogen is chlorine.

11. Pharmaceutical composition according to claim 8, characterized by being in form suitable for the administration by intravenous or intramuscular route.

12. A method of treating hyperlipidemia in a patient in need of such treatment comprising administering to the patient an anti-hyperlipidemically effective amount of a diacylester of glycerylphosphorylcholine according to claim 1.

* * * * *